United States Patent [19]

Palmskog

[11] Patent Number: 5,507,737
[45] Date of Patent: Apr. 16, 1996

[54] APPARATUS FOR DETERMINING THE VOLUME OF A BELLOWS RESERVOIR FOR MEDICATION IN AN IMPLANTABLE INFUSION SYSTEM

[75] Inventor: Goeran Palmskog, Jaerfaella, Sweden

[73] Assignee: Siemens Elema AB, Solna, Sweden

[21] Appl. No.: 231,311

[22] Filed: Apr. 22, 1994

[30] Foreign Application Priority Data

Apr. 22, 1993 [SE] Sweden ................................. 9310344

[51] Int. Cl.⁶ .......................... A61M 11/00; A61M 1/00; A61K 9/22
[52] U.S. Cl. .................. 604/891.1; 604/93; 604/118; 128/DIG. 13; 128/903
[58] Field of Search ............................ 604/891.1, 93, 604/151, 153, 65–67, 246, 118; 128/DIG. 12, DIG. 13, 903

[56] References Cited

U.S. PATENT DOCUMENTS

| | | | |
|---|---|---|---|
| 4,360,019 | 11/1982 | Portner et al. | |
| 4,373,527 | 2/1983 | Fischell | 604/891.1 |
| 4,395,259 | 7/1983 | Prestele et al. | 604/67 |
| 4,443,218 | 4/1984 | DeCant, Jr. et al. | 604/67 |
| 4,447,244 | 5/1984 | DeCant, Jr. et al. | 604/67 |
| 4,464,172 | 8/1984 | Lichtenstein | 604/65 |
| 4,486,190 | 12/1984 | Reinicke | 604/67 |
| 4,557,726 | 12/1985 | Reinicke | 604/67 |
| 4,573,994 | 3/1986 | Fischell et al. | 604/891 X |
| 4,717,462 | 12/1987 | DiDomenico | 604/67 |
| 4,871,351 | 10/1989 | Feingold | 604/66 |

FOREIGN PATENT DOCUMENTS

WO89/01795  4/1993  WIPO .

*Primary Examiner*—John D. Yasko
*Assistant Examiner*—Adam J. Cermak
*Attorney, Agent, or Firm*—Hill, Steadman & Simpson

[57] ABSTRACT

In a method and apparatus for determining the volume of a bellows reservoir for medication in an infusion system which is implantable in a patient, the pressure in the reservoir is measured and the corresponding volume is determined from a predetermined relationship between pressure and volume. A pressure gauge is disposed for measuring the pressure in the bellows reservoir, and a signal corresponding to the measured pressure is supplied to a memory unit wherein a corresponding volume is determined from the measured pressure value by means of the predetermined relationship between pressure and volume being stored in the memory unit.

6 Claims, 2 Drawing Sheets

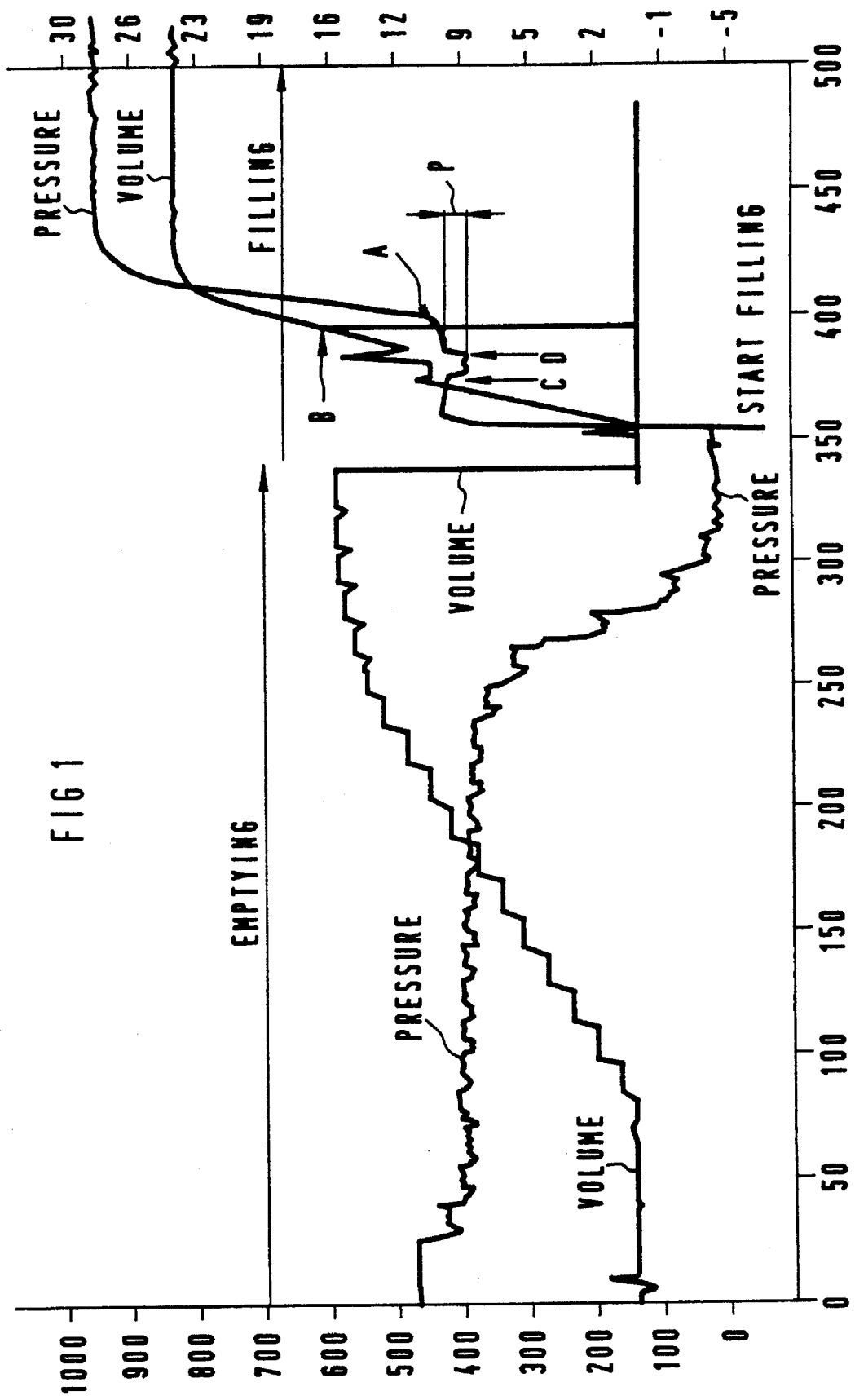

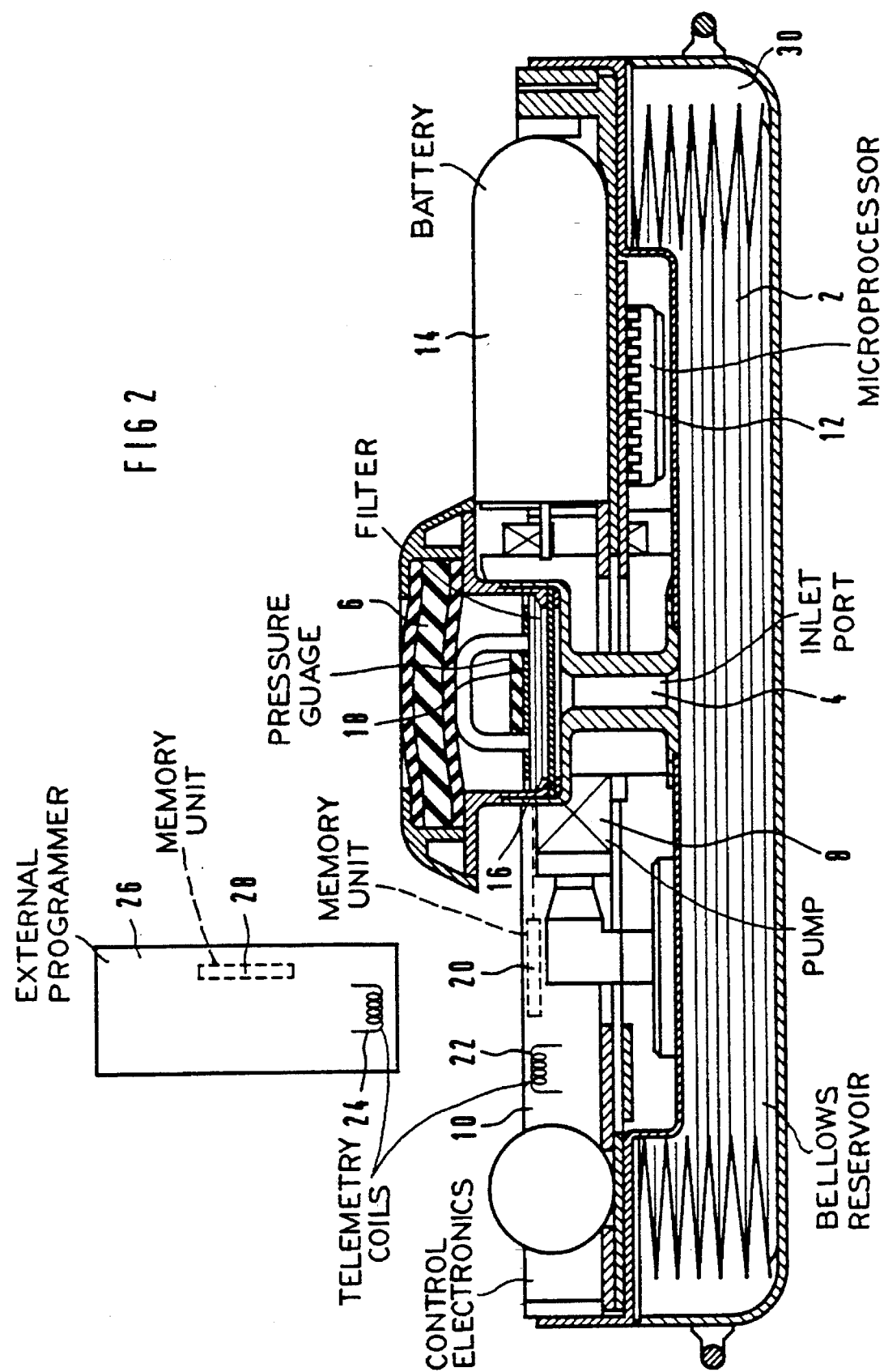

5,507,737

APPARATUS FOR DETERMINING THE VOLUME OF A BELLOWS RESERVOIR FOR MEDICATION IN AN IMPLANTABLE INFUSION SYSTEM

BACKGROUND OF THE INVENTION

1. Field of the Invention

The present invention is directed to a method and to an apparatus for determining the volume of a bellows reservoir for medication in an implantable infusion system.

2. Description of the Prior Art

In an implantable infusion system, wherein medication to be dispensed is contained in a reservoir, there is a need to continuously determine the volume of medication in the reservoir. This is for at least two reasons, first, it must be ensured that the medication volume in the reservoir does not become too low before a medication refilling procedure is undertaken, otherwise air, which is always present in the reservoir, would then be pumped into the patient. Second, because the pressure in the bellows reservoir decreases as the medication volume becomes less than 2–3 ml, if the medication volume reaches such a low level the pump must operate with a larger pressure difference, resulting in reduced medication volume per pump stroke, leading to cavitation in the pump. Such cavitation is detrimental to medications like insulin, whose molecules are "fragile."

Moreover, it is desirable to be able to determine the volume of the medication in the bellows reservoir during a filling procedure, in order to avoid overfilling the reservoir. The bellows reservoir is contained in the implantable unit in a chamber which creates appropriate pressure conditions for siphoning medication from a refilling apparatus which is temporarily placed in fluid communication with the implanted unit during the refilling procedure. If the bellows reservoir is overfilled to the extent that the bellows wall comes into contact with the wall of the chamber, the conditions for siphoning are no longer present.

SUMMARY OF THE INVENTION

It is an object of the present invention to provide a method and an apparatus for continuously determining the volume of a bellows reservoir for medication during operation of an infusion system, as well as during emptying and filling of the reservoir.

The above object is achieved in a method for determining the volume of a bellows reservoir for medication in an implantable infusion system by measuring the pressure which is exclusively present in the reservoir, and determining the corresponding volume from a predetermined relationship between pressure and volume.

The above object is also achieved in an apparatus which includes a pressure gauge disposed for measuring the pressure exclusively in the reservoir, the pressure gauge generating an output signal corresponding to the measured pressure, which is supplied to a memory unit in which a predetermined relationship between pressure and volume is stored. Based on the stored relationship, the memory unit generates an output representing the volume corresponding to the measured pressure.

As used herein, the references to measuring the pressure which is exclusively present in the reservoir are meant to exclude measurements, for example, of the pressure prevailing generally within the implantable housing. Measuring the pressure which is exclusively present in the reservoir means undertaking a measurement of the pressure which exists within the reservoir itself, rather than a measurement of the pressure prevailing in the "environment" of the reservoir.

In a further embodiment of the method, the predetermined relationship between pressure and volume is determined by simultaneous measurement of the pressure versus volume curves which arise during filling and emptying of the reservoir. Using these curves, the relationship of volume and pressure can then be determined.

The pressure gauge is preferably disposed in the filler port of the reservoir, and may be a piezoelectric gauge.

The memory unit in which the predetermined relationship between volume and pressure is stored, is preferably disposed in an external programmer, outside of the patient and separate from the implanted unit, which communicates with the implanted unit, at least to the extent of receiving output signals from the pressure gauge, by telemetry.

DESCRIPTION OF THE DRAWINGS

FIG. 1 shows typical pressure-volume curves which arise when emptying residual insulin from, and filling fresh insulin into, an implantable insulin infusion system.

FIG. 2 is a side sectional view through an implantable unit of an infusion system constructed in accordance with the principles of the present invention, the infusion system also including a schematically-indicated external programmer.

DESCRIPTION OF THE PREFERRED EMBODIMENTS

FIG. 1 shows typical pressure-volume curves which arise when emptying residual insulin from, and filling fresh insulin into, an implantable insulin infusion system, of the type shown in FIG. 2. The pressure can be recorded by means of a pressure gauge introduced with a cannula through the septum 6 to about the same level as the pressure gauge 18 of the apparatus according to the invention, described below, during emptying and filling of carefully determined volumes of insulin. This calibration procedure has been verified for fifteen reservoirs.

The relationship between pressure and volume can obviously vary for different types of reservoirs. The example illustrated in FIG. 1 relates to a bellows reservoir having a volume of approximately 24 ml.

As can be seen in FIG. 1, the pressure curve which arises when emptying the reservoir has a plateau at about 400 mbar. The level for this plateau is dependent on the temperature at which the emptying takes place. For an infusion system implanted for animal tests, the temperature was 38° C., in which case the plateau will be situated at about 700 mbar.

When 2–3 ml of insulin remain in the reservoir, the pressure within the reservoir begins to decrease below the plateau pressure, and to empty the last 2–3 ml of insulin from the reservoir the pressure must be lowered to less than 100 mbar. This appears to be the case for all examined bellows reservoirs of the type in question. At a pressure of 50 mbar, there is still 0.5–1 ml of insulin remaining in the reservoir. A pressure gauge which has a pressure threshold of approximately 600 mbar will, for normal body temperature, identify when the volume of the residual insulin drops to 2–3 ml, which is suitable in practice. If the volume of residual insulin drops below this level, the pump must operate against too low a pressure differential, and cavitation problems will occur.

Also, there is a need for continuously recording the pressure when filling the reservoir. Typically, the reservoir is filled from a refilling system which is temporarily connected by means of a cannula to the implanted unit, with the conditions for siphoning medication from the refilling system to the implanted unit being present. The conditions for siphoning are no longer present when the bellows wall comes into contact with the wall of the implanted housing. To the right in FIG. 1, the pressure-volume curves are shown which arise during filling of the reservoir. From these curves, it can be seen that the specified depressurization of 450 mbar in this case, at A on the pressure curve, can no longer be maintained when the bellows reservoir is filled to approximately 17 ml, at B on the volume curve. From point A, the pressure steeply increases. This rapid pressure increase illustrates the need for continuously monitoring the pressure during the filling phase, and the apparatus according to the invention is preferably equipped with an alarm which is activated when the pressure in the bellows reservoir becomes too high. It is also preferable to have this alarm operative when the pump of the infusion system is in operation. This is because if leakage occurs, this can result in the bellows coming into contact with leaked fluid disposed between the bottom of the bellows and the housing wall, thereby resulting in the same situation as described above due to overfilling. The pressure as a function of the volume of the bellows reservoir will progress identically during emptying and filling.

FIG. 2 shows a cross section through an implantable unit of an infusion system for which the curves shown in FIG. 1 have been recorded, and also schematically shows the external programmer which is used as part of the infusion system together with the implantable unit.

The implantable unit includes a bellows reservoir 2 for medication, such as insulin, having an inlet port 4, closed by the septum 6. The implantable unit also contains a pump 8, control electronics 10, a microprocessor 12 and a battery 14. A filter 16 is disposed in the inlet port 4, and a pressure gauge 18 is mounted adjacent the filter 16. The bellows reservoir is contained in a chamber 30.

The pressure gauge 18 may be any type of commercially available piezoelectric pressure sensor. The pressure gauge 18 is connected to a memory unit 20, as part of the control electronics 10, wherein the relationship between pressure and volume is stored, this relationship being determined in advance as described above. The implantable unit includes a telemetry coil 22 (connected to telemetry circuitry as part of the control electronics 10, not separately shown) and the external programmer 26, includes a telemetry coil 24. Communication between the implanted unit and the programmer 26 is therefore established, at least to the extent of permitting the pressure as measured by the pressure gauge 18 to be transmitted in the form of a telemetry signal from the implanted unit to the external programmer 26. Through the telemetry link established by the coils 22 and 24, pressure and/or volume values can be continuously transmitted for external recording.

Further details of the structure of the pressure gauge 18, the memory unit 20 and the telemetry coil 22 are not shown, since these are individually well-known to those skilled in the art. The memory unit 20, instead of being a part of the control electronics 10 the implanted unit, can be disposed in the external programmer 26, as schematically indicated by the memory unit 28 shown in dashed lines therein.

In the exemplary embodiment of FIG. 2, the pressure gauge 18 is shown positioned in the inlet port 4 to the bellows reservoir 2. The pressure gauge 18, however, can be disposed at a number of different places relative to the bellows reservoir 2, as long as the pressure gauge 18 measures the pressure which is exclusively present in the bellows reservoir. For example, if the pressure gauge 18 is suitably disposed for measuring a pressure drop which occurs across the filter 16, the output signals from the pressure gauge 18 can, in addition to the aforementioned purpose of indicating the volume of the bellows reservoir 2, be used to provide an indicator as to when the filter 16 has become clogged. Clogging of the filter 16 makes movement of the insulin through the filter 16 difficult in both directions. The pressure drop across the filter 16 becomes larger with increased clogging of the filter 16.

FIG. 1 shows a rapid pressure drop at C, which arises as the filling flow is stopped, and a corresponding rapid pressure increase is shown at D, as the filling flow is started again. This pressure differential $\Delta p$ precisely corresponds to the pressure drop cross the filter 16.

Although modifications and changes may be suggested by those skilled in the art, it is the intention of the inventor to embody within the patent warranted hereon all changes and modifications as reasonably and properly come within the scope of his contribution to the art.

I claim as my invention:

1. In an implantable infusion system having a bellows reservoir for containing medication to be infused, said bellows reservoir having an inlet port, the improvement of an apparatus for determining the volume of said bellows reservoir, said apparatus comprising:

pressure gauge means for measuring a pressure which is present exclusively in said bellows reservoir, and for generating a signal corresponding to the measured pressure; and means for storing a predetermined relationship between pressure and volume of said bellows reservoir, to which said signal from said pressure gauge means is supplied, and for generating a signal identifying a volume corresponding to said measured pressure.

2. An apparatus as claimed in claim 1 wherein said pressure gauge means is disposed in said inlet port.

3. An apparatus as claimed in claim 1 wherein said pressure gauge means comprises a piezoelectric pressure sensor.

4. An apparatus as claimed in claim 1 further comprising alarm means, connected to receive said signal from said pressure gauge means, for generating an alarm if said measured pressure exceeds a predetermined level.

5. An apparatus as claimed in claim 1 further comprising alarm means, connected to receive said signal from said pressure gauge means, for generating an alarm if said measured pressure falls below a predetermined level.

6. A medical infusion system comprising:

a bellows reservoir for containing medication to be infused;

pressure gauge means for measuring a pressure which is present exclusively in said bellows reservoir, and for generating a signal corresponding to the measured pressure;

means for storing a predetermined relationship between pressure and volume of said bellows reservoir, to which said signal from said pressure gauge means is supplied, and for generating a signal identifying a volume corresponding to said measured pressure;

an implantable unit in which said bellows reservoir and said pressure gauge means are contained;

an external programmer in which said means for storing said predetermined relationship is contained; and means for telemetrically communicating between said pressure gauge means and said means for storing said predetermined relationship.

* * * * *